United States Patent [19]

Nagubandi

[11] 4,439,373

[45] Mar. 27, 1984

[54] PROCESS FOR PREPARING PHOSPHONOMETHYLATED AMINO ACIDS

[75] Inventor: Sreeramulu Nagubandi, Bedford Hills, N.Y.

[73] Assignee: Stauffer Chemical Company, Westport, Conn.

[21] Appl. No.: 453,661

[22] Filed: Dec. 27, 1982

[51] Int. Cl.³ .................................................. C07F 9/38
[52] U.S. Cl. .......................... 260/502.5 F; 260/465.2; 260/938; 260/941; 560/155; 560/157; 562/555
[58] Field of Search ...................... 260/502.5 F, 465.2; 560/155

[56] References Cited

U.S. PATENT DOCUMENTS

| | | | |
|---|---|---|---|
| 3,956,370 | 5/1976 | Parry et al. | 260/502.5 F |
| 4,063,491 | 12/1977 | Pfliegel et al. | 260/502.5 F |
| 4,233,056 | 11/1980 | Maier | 260/502.5 F |
| 4,251,258 | 2/1981 | Kaufman | 260/502.5 F |

FOREIGN PATENT DOCUMENTS

| | | | |
|---|---|---|---|
| 55695 | 7/1982 | European Pat. Off. | 260/502.5 F |
| 1436844 | 5/1976 | United Kingdom | 260/502.5 F |

*Primary Examiner*—J. E. Evans

[57] ABSTRACT

A process for preparing phosphonomethylated amino acids comprising protecting a primary amino acid ester or salt with a carbon dioxide protecting group, phosphonomethylating the protected amino compound formed, and removing the carbon dioxide protecting group by acidification.

18 Claims, No Drawings

PROCESS FOR PREPARING PHOSPHONOMETHYLATED AMINO ACIDS

FIELD OF THE INVENTION

The present invention is a process for preparing phosphonomethylated amino acids and, in particular, for preparing N-phosphonomethylglycine, otherwise known as glyphosate.

BACKGROUND OF THE INVENTION

Glyphosate and its derivatives are herbicides. Herbicides are useful for controlling or modifying plant growth. Glyphosate and its derivatives are effective in controlling or modifying growth in a wide variety of plant species, including broadleaves, grasses and sedge.

Because glyphosate and its derivatives are so useful, new processes for making it and its derivatives faster, cheaper or in greater yields are constantly in demand. A new process for preparing glyphosate and its derivatives has now been discovered.

PRIOR ART

When ammonia is reacted with α-halogen acids, the resultant product is a mixture of primary, secondary and tertiary amino acids. It is postulated that the primary amino acid is formed first, that some of the primary amino acids then react with additional α-halogen acids to form secondary amino acids, and finally, that some of the secondary amino acids react with more α-halogen acids to form tertiary amino acids. In many cases only one of these amino acids is the desired product and elaborate separation procedures are required.

If the desired product is a primary amino acid, the preparation of secondary and tertiary amino acids can be prevented by attaching a deactivating group to the nitrogen of ammonia to form a protected amino compound. The deactivating group may be carbon dioxide. The deactivating group allows the protected amino compound to react once with α-halogen acids and then prevents the protected amino compound from further reaction. As a result, no significant amounts of secondary or tertiary amino acids are formed. The deactivating group can easily be removed after the reaction with α-halogen acid is complete.

The following reaction is typical. Under ordinary circumstances, $$2NH_3 + ClCH_2CO_2H \longrightarrow H_2NCH_2CO_2H + NH_4Cl \quad (1)$$
(1° amino acid)

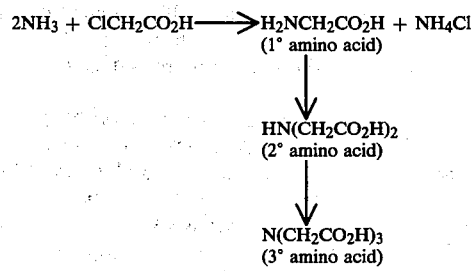

If only the primary amino acid is desired, the reaction can be carried out using a large excess of ammonia in the presence of carbon dioxide and/or sodium bicarbonate. In this way, the amine group reacts first with carbon dioxide to form a protected amino compound and then once with α-halogen acids. The reaction conditions are such that further reaction of the amine with the acids is inhibited. The protecting group, which is CO₂, is removed from the protected amino compound by acidification. The following sequence is postulated.

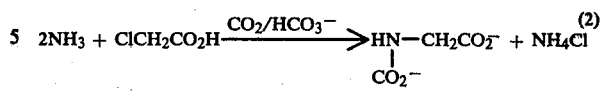

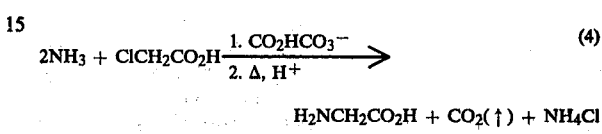

The entire reaction ((2) and (3)) may be carried out in one pot, so that $$2NH_3 + ClCH_2CO_2H \xrightarrow[2.\ \Delta,\ H^+]{1.\ CO_2HCO_3^-} \quad (4)$$

$$H_2NCH_2CO_2H + CO_2(\uparrow) + NH_4Cl$$

BRIEF DESCRIPTION OF THE INVENTION

It has now been discovered that the amine group of a primary amino acid or similar compound can be protected with carbon dioxide so that phosphonomethylated secondary amino acids can be obtained. Glyphosate is an example of a phosphonomethylated secondary amino acid.

The reaction to prepare phosphonomethylated secondary amino acids is carried out in three steps. In the first step, a primary amino acid is converted to a salt or an ester and this salt or ester is reacted with a carbon dioxide source to form a protected amino compound. Alternatively, an amino acid salt, amino acid ester or other substituted primary amine may be used directly to form a protected amino compound. In the second step, the protected amino compound is phosphonomethylated in basic solution with formaldehyde and a phosphorous source to give a phosphonomethylated protected amino compound. Finally, the protecting group is removed from the phosphonomethylated protected amino compound to give a phosphonomethylated secondary amino acid. The following sequence is exemplary:

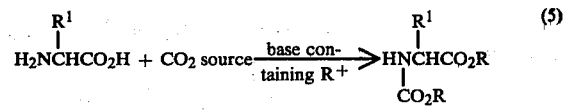

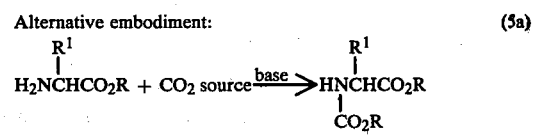

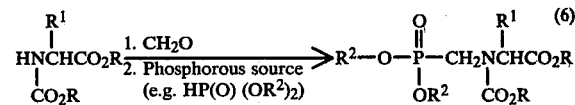

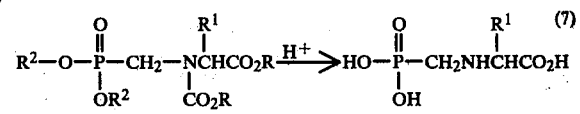

In each of reactions (5) and (5a), the CO₂ source is selected from the group consisting of a carbonate salt, a bicarbonate salt or carbon dioxide gas. In reaction (5), the base is, for example, sodium hydroxide or barium hydroxide.

In a reaction (5), R is selected from the group consisting of an alkali metal; an alkaline earth metal; ammonium; and an organic ammonium cation. In each of reactions (5a), (6) and (7), R is selected independently each time it occurs from the group consisting of an alkali metal; an alkaline earth metal; ammonium; an organic ammonium cation; alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and chloro. In each of reactions (5) (5a), (6) and (7), $R^1$ is selected from the group consisting of hydrogen; a primary or secondary aliphatic alkyl having 1 to 8 carbon atoms, inclusive, alkenyl having 2 to 8 carbon atoms, inclusive and alkynyl having 2 to 8 carbon atoms, inclusive, wherein said alkyl, alkenyl or alkynyl may be optionally substituted with a member of the group consisting of halogen; a hydroxy group; an amine; a cyano group; a carboxy group; alkoxy having 1 to 4 carbon atoms, inclusive; an amido group; a thio group; a sulfide group having 1 to 4 carbon atoms, inclusive; aryloxy having 6 to 12 carbon atoms, inclusive; alkoxy carbonyl having 1 to 8 carbon atoms, inclusive; phenyl; aryl having 6 to 12 carbon atoms, inclusive; carboxyaryl having 7 to 12 carbon atoms, inclusive; amino alkyl amine having 1 to 8 carbon atoms, inclusive; alkoxyalkoxy having 2 to 8 carbon atoms, inclusive; and a heterocyclic group having 2 to 12 carbon atoms, inclusive.

In reaction (6), the phosphorous source is selected from the group consisting of

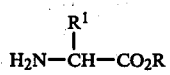

wherein $R^2$ is selected independently each time it occurs from the group consisting of alkyl having 1 to 8 carbon atoms, inclusive; phenyl; and substituted phenyl; wherein the substituents are selected from the group consisting of alkyl having 1 to 4 carbon atoms, inclusive; alkoxy having 1 to 4 carbon atoms, inclusive; and halogen. In certain limited circumstances, $R^2$ is hydrogen.

When $R^1$ is hydrogen, the resulting product is glyphosate.

DETAILED DESCRIPTION OF THE INVENTION

In the first step of this process a primary amino acid is converted to a salt or an ester, and then this salt or ester is reacted with a protecting group to form a protected amino compound. The primary amino acid may have the structure

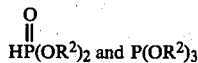

wherein $R^1$ is selected from the group consisting of hydrogen, a primary or secondary aliphatic alkyl having 1 to 8 carbon atoms, inclusive, alkenyl having 2 to 8 carbon atoms, inclusive and alkynyl having 2 to 8 carbon atoms, inclusive, wherein said alkyl, alkenyl or alkynyl are optionally substituted with a member of the group consisting of halogen; a hydroxy group; an amine; a cyano group; a carboxy group; alkoxy having 1 to 4 carbon atoms, inclusive; an amido group; a thio group; a sulfide group having 1 to 4 carbon atoms, inclusive; aryloxy having 6 to 12 carbon atoms, inclusive; alkoxy carbonyl having 1 to 8 carbon atoms, inclusive; phenyl; aryl having 6 to 12 carbon atoms, inclusive; carboxyaryl having 7 to 12 carbon atoms, inclusive; amino alkyl amine having 1 to 8 carbon atoms, inclusive; alkoxyalkoxy having 2 to 8 carbon atoms, inclusive; and a heterocyclic group having 2 to 12 carbon atoms, inclusive. In a preferred embodiment, $R^1$ is hydrogen.

The acid is converted to a salt or an ester before it is reacted with a protecting group. The salt may be made by using an excess of the protecting group source if the source is appropriate for forming a salt or by using a separate base, such as sodium hydroxide or barium hydroxide. The ester may be prepared by dissolving the acid in a simple alcohol, such as ethanol, and heating it in the presence of anhydrous hydrochloric acid.

Alternatively, an amino acid salt or amino acid ester may be used as a starting material for this process, making the conversion described above unnecessary. Such a salt or ester may have the structure

wherein R is selected from the group consisting of an alkali metal; an alkaline earth metal; ammonium; an organic ammonium cation; alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and chloro and $R^1$ is as defined above. An example of a suitable ester is glycine ethyl ester (R is ethyl and $R^1$ is hydrogen), which is commercially available as glycine ethyl ester hydrochloride.

The reaction of amino acid salt, amino acid ester or other suitable primary amine and a protecting group is carried out in a suitable solvent. Suitable solvents include water or organic solvents. Examples of suitable organic solvents include but are not limited to, dimethylsulfoxide or simple alcohols, such as methanol or ethanol.

The protecting group is carbon dioxide. The carbon dioxide protecting group is obtained from a source such as a carbonate salt, a bicarbonate salt or carbon dioxide gas. In a preferred embodiment, the protecting group source is sodium bicarbonate, sodium carbonate or carbon dioxide gas.

To form a protected amino compound, the mole ratio of amino acid to protecting group should be at least 1 to 1, i.e., for every mole of amino acid which is used, at least one mole of protecting group should be used. However, a two or three times excess of the protecting group, i.e., two or three moles of protecting group for every mole of amino acid, may be beneficial to drive the reaction to completion.

When the source of the protecting group is sodium bicarbonate or sodium carbonate, the amino acid may be converted to a salt and the salt reacted with the protecting group in one step. This is accomplished by using at least a two times and up to about a five times excess of sodium bicarbonate, i.e., at least two moles and up to about five moles of sodium bicarbonate for every mole of amino acid. In this way, one mole of the sodium bicarbonate may be used to convert the acid to a salt and the remainder may be reacted with the amino acid salt to form a protected amino compound. Alternatively, at least one mole and up to about five moles of sodium carbonate may be used for every mole of amino acid. Greater amounts of sodium bicarbonate or sodium carbonate are undesirable for economic reasons.

The amino acid and sodium bicarbonate or sodium carbonate may be combined in a reaction flask at room temperature or below with stirring. If the protecting group is present in greater concentrations than the amino acid, heating to a temperature less than 100° C. may be required to dissolve the excess salt.

If the source of the protecting group is gaseous, the reaction conditions are similar, i.e., room temperature or below with stirring, but the gas may be bubbled through the reaction mixture at one atmosphere pressure or higher. In this case it is desirable to form the amino acid salt prior to bubbling the gas through the mixture. This is done by adding a base, such as sodium hydroxide or barium hydroxide, to the amino acid.

As an alternative means of converting the amino acid to a salt and converting the salt to a protected amino compound, sodium bicarbonate is used followed by carbon dioxide gas. This method can insure that the reaction goes to completion.

In a second alternative embodiment, the protected amino compound may be formed directly from ammonia by reacting ammonia with chloroacetic acid in the presence of carbon dioxide or bicarbonate. Other routes for forming the protected amino compound are also possible.

Once the protected amino compound is formed, it may be isolated. The protected amino compound may be phosphonomethylated in basic media. The phosphonomethylation may be carried out by adding formaldehyde and a phosphorous source to the protected amino compound to form a phosphonomethylated protected amino compound.

Additionally, the phosphonomethylation may be carried out either with or without a carbon dioxide atmosphere. If a carbon dioxide atmosphere is used, the pressure can range from about 1 to about 50 atmospheres, and is preferably in the range of about 1 to about 5 atmospheres.

The formaldehyde may be used in the form of aqueous formaldehyde or solid paraformaldehyde. If solid paraformaldehyde is used water can be used as a solvent. The mole ratio of formaldehyde to protected amino compound should be at least 1:1. Excess amounts of formaldehyde, up to a 3:1 mole ratio, can be employed. Mole ratios of greater than 3:1 are not desirable for economic reasons.

The formaldehyde may be slowly added to the protected amino compound at temperatures in the range of about 1° C. to about 30° C. The reaction mixture may exotherm by a temperature of about 1° to 5° C.

Water may be added to dissolve the protected amino compound and/or to facilitate stirring. The protected amino compound having a carbon dioxide protecting group will form a solution having a pH of about 9 or 10 when dissolved in water. The water may be added either before or after the addition of formaldehyde.

In an alternative embodiment, the protected amino compound is suspended in an organic solvent, such as methanol. If this is done, it may be necessary to make the reaction mixture basic with a suitable base before adding formaldehyde to the protected amino compound. Suitable bases include, but are not limited to, sodium hydroxide, sodium methoxide and sodium ethoxide.

After the formaldehyde is added, the reaction mixture may be stirred for about a half hour or more at room temperature or at a temperature up to about 50°–60° C. In a preferred embodiment the reaction mixture is stirred at room temperature for about one hour.

The phosphorous source may have the structure

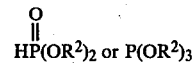

wherein $R^2$ is selected independently each time it occurs from the group consisting of alkyl having 1 to 8 carbon atoms, inclusive; phenyl; and substituted phenyl wherein the substituents are selected from the group consisting of alkyl having 1 to 4 carbon atoms, inclusive; alkoxy having 1 to 4 carbon atoms, inclusive; and halogen. In certain limited circumstances, $R^2$ is hydrogen.

The mole ratio of phosphorous source to protected amino compound should also be at least 1:1 and can range up to about 2:1. Greater amounts of the phosphorous source relative to the protected amino compound are not economically desirable. The phosphorous source is added to the flask containing the protected amino compound and formaldehyde. This reaction mixture is heated to reflux at about 95° C. for at least 2 to 3 hours. The refluxing may be carried out under carbon dioxide atmosphere.

In an alternative embodiment, the formaldehyde is reacted in basic media and the phosphorous source is reacted in acidic media. This embodiment can be ussed when the ratio of formaldehyde to protected amino compound is 1:1 and the reaction goes to completion. Acidification of the reaction mixture will expel the carbon dioxide protecting group prior to reacting with the phosphorous source.

Any acid may be used to acidify the reaction mixture before adding the phosphorous source. Such acids include, but are not limited to, hydrochloric acid, hydrobromic acid, sulfuric acid, acetic acid, nitric acid and perchloric acid. Following the acidification, the phosphorous source may be added as described. Alternatively, phosphorous acid may be used both to acidify the reaction mixture and as a phosphorous source.

If the phosphonomethylation has been carried out entirely in basic media, reaction mixture containing the phosphonomethylated protected amino compound is acidified to expel the protecting group. Any acid may be used for this purpose. Such acids include but are not limited to hydrochloric acid, hydrobromic acid, sulfuric acid, acetic acid, nitric acid and perchloric acid.

It may be necessary to remove other groups in addition to the protecting group, depending on the particular phosphorous source and primary amino acid derivative used. If alkyl groups must be removed in addition to the protecting group, strong acids, such as the first two listed, should be used and the reaction mixture is heated to reflux for at least 3 to 10 hours. If phenyl groups must be removed, this is done in the presence of an acid as described above or a base, such as sodium hydroxide.

The resulting product is a phosphonomethylated secondary amino acid. The following Examples show a practical application of the process described. The final product obtained in each Example is glyphosate. ($R^1$ is hydrogen in equations (5), (5a), (6) and (7).)

EXAMPLE 1

To a solution of glycine (37.5 g, 0.5 mole) in water (200 ml), anhydrous sodium carbonate (53 g, 0.5 mole) in water (200 ml) was added and the reaction was stirred at room temperature. After 0.5 hour, a small amount of insoluble particles were filtered and methanol (2.0 L) was added. The resulting disodium glycine carbamate ($NaO_2CNHCH_2CO_2Na$) was filtered and washed with ether (50 ml). The moist solid was dried under vacuum at 60°–70° C. for 3 hours to obtain 64 g (77%) of anhydrous white solid (disodium glycine carbamate).

To a solution of disodium glycine carbamate (13.6 g, 0.083 mole) in water (50 ml), 37% aqueous formaldehyde (10.1 ml, 3.74 g, 0.125 mole) was added. The reaction was slightly exothermic. After stirring the reaction mixture, for 0.5 hour, at room temperature, diethyl phosphite (16.98 g, 0.123 mole) was added. The reaction mixture was heated to 95° C. for 2 hours. After cooling the reaction mixture, ethanol (100 ml) was added and the solvent was removed under vacuum. The resulting oil was acidified to pH 2 with concentrated hydrochloric acid. Sodium chloride was filtered off. The remaining reaction mixture contained 16.4 g of diethylphosphonomethyl glycine.

Diethylphosphonomethyl glycine (6 g) was refluxed, for 16 hours, with concentrated hydrochloric acid (20 ml). The reaction mixture was cooled and the solvent was evaporated to obtain glyphosate, which was confirmed by high pressure liquid chromatograph and $^{31}$P-nuclear magnetic resonance and infrared spectra.

EXAMPLE 2

To a solution of barium hydroxide (160 g, 0.93 mole) in water (3.5 L), a solution of glycine (37.5 g, 0.5 mole) in water (200 ml) was added. After adding phenolphthalein (several drops), carbon dioxide gas was bubbled into the reaction mixture, at a constant rate, until the pink color of the indicator disappeared. The reaction mixture was cooled and filtered to obtain 105 g (84%) glycine carbamate barium salt ($Ba^{++}$ $^-O_2CNHCH_2CO_2^-$)

The balance of this Example has not been carried out with the glycine carbamate barium salt prepared above, but it is expected that it would work as described.

Glycine carbamate salt is suspended in anhydrous ethanol and the pH is adjusted to 9 with sodium ethoxide. Paraformaldehyde (1.1 mole eg.) is added. Triethyl phosphite (1.1 mole eg.) is added and the reaction mixture is heated at reflux for about 3 hours. The solvent is evaporated and the resulting crude mixture is acidified using concentrated hydrochloric acid, to obtain diethylphosphonomethyl glycine which is later hydrolyzed, as described in Example 1, to glyphosate.

What is claimed is:

1. A process for preparing phosphonomethylated amino acids comprising:
   reacting a primary amino acid ester or salt with a carbon dioxide protecting group to form a protected amino compound;
   phosphonomethylating said protected amino compound to obtain a phosphonomethylated protected amino compound; and
   acidifying said phosphonomethylated protected amino compound to expel said carbon dioxide protecting group and yield a phosphonomethylated amino acid or acid derivative.

2. A process as defined in claim 1 wherein said primary amino acid ester or salt has the structure

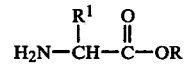

wherein R is selected from the group consisting of an alkali metal; an alkaline earth metal; ammonium; an organic ammonium cation; alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and chloro and, $R^1$ is selected from the group consisting of hydrogen, a primary or secondary aliphatic alkyl having 1 to 8 carbon atoms, inclusive, alkenyl having 2 to 8 carbon atoms, inclusive and alkynyl having 2 to 8 carbon atoms, inclusive, wherein said alkyl, alkenyl or alkynyl are optionally substituted with a member of the group consisting of halogen; a hydroxy group; an amine; a cyano group; a carboxy group; alkoxy having 1 to 4 carbon atoms, inclusive; an amido group; a thio group; a sulfide group having 1 to 4 carbon atoms, inclusive; aryloxy having 6 to 12 carbon atoms, inclusive; alkoxy carbonyl having 1 to 8 carbon atoms, inclusive; phenyl; aryl having 6 to 12 carbon atoms, inclusive; carboxyaryl having 7 to 12 carbon atoms, inclusive; amino alkyl amine having 1 to 8 carbon atoms, inclusive; alkoxyalkoxy having 2 to 8 carbon atoms, inclusive; and a heterocyclic group having 2 to 12 carbon atoms, inclusive.

3. A process as defined in claim 2 wherein $R^1$ is hydrogen.

4. A process as defined in claim 1 wherein said carbon dioxide protecting group is selected from a source consisting of sodium bicarbonate, sodium carbonate and carbon dioxide gas.

5. A process as defined in claim 4 wherein said primary amino acid ester or salt is reacted with one mole equivalent of said carbon dioxide protecting group.

6. A process as defined in claim 1 wherein said protected amino compound is phosphonomethylated using formaldehyde and a phosphorous source.

7. A process as defined in claim 6 wherein said formaldehyde is used in the form of aqueous formaldehyde.

8. A process as defined in claim 6 wherein said phosphorous source has the structure

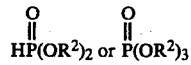

wherein $R^2$ is selected independently each time it occurs from the group consisting of alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen.

9. A process as defined in claim 6 wherein said protected amino compound is phosphonomethylated in basic media.

10. A process as defined in claim 9 wherein said phosphonomethylation is carried out under carbon dioxide at pressures in the range of about 1 to about 5 atmospheres.

11. A process as defined in claim 6 wherein said protected amino compound is phosphonomethylated using formaldehyde in basic media and a phosphorous source in acidic media.

12. A process as defined in claim 1 wherein said phosphonomethylated protected amino compound is acidified with an acid selected from the group consisting of hydrochloric acid, hydrobromic acid, sulfuric acid, acetic acid, nitric acid and perchloric acid.

13. A process as defined in claim 1 wherein acidification of said phosphonomethylated protected amino compound yields a phosphonomethylated amino acid derivative and said derivative is hydrolyzed to a phosphonomethylated amino acid by heating in acid.

14. A process for preparing glyphosate comprising:
reacting glycine with sodium bicarbonate or sodium carbonate to form a protected amino compound;
phosphonomethylating said protected amino compound using formaldehyde and a phosphorous source to obtain a phosphonomethylated protected amino compound;
acidifying said phosphonomethylated protected amino compound to expel said carbon dioxide protecting group and form a phosphonomethylated amino compound; and
heating said phosphonomethylated amino compound in the presence of acid to hydrolyze any ester groups and to yield glyphosate.

15. A process as defined in claim 14 wherein said phosphorous source has the structure

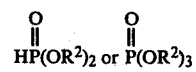

wherein $R^2$ is selected independently each time it occurs from the group consisting of an alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen.

16. A process as defined in claim 15 wherein said protected amino compound is phosphonomethylated in basic media.

17. A process as defined in claim 15 wherein said protected amino compound is phosphonomethylated using formaldehyde in basic media and a phosphorous source in acidic media.

18. A process as defined in claim 14 wherein said phosphonomethylated protected amino compound is acidified with an acid selected from the group consisting of hydrochloric acid, hydrobromic acid, sulfuric acid, acetic acid, nitric acid and perchloric acid.

* * * * *